(12) United States Patent
Bai et al.

(10) Patent No.: US 11,370,834 B2
(45) Date of Patent: Jun. 28, 2022

(54) ANTI-VEGFR-2 MONOCLONAL ANTIBODY

(71) Applicant: BEIJING DONGFANG BIOTECH CO., LTD., Beijing (CN)

(72) Inventors: Yi Bai, Beijing (CN); Xiangguo Gu, Beijing (CN)

(73) Assignee: BEIJING DONGFANG BIOTECH CO., LTD., Beijing (CN)

( * ) Notice: Subject to any disclaimer, the term of this patent is extended or adjusted under 35 U.S.C. 154(b) by 245 days.

(21) Appl. No.: 16/487,833

(22) PCT Filed: Feb. 14, 2018

(86) PCT No.: PCT/CN2018/076847
§ 371 (c)(1),
(2) Date: Aug. 22, 2019

(87) PCT Pub. No.: WO2018/161798
PCT Pub. Date: Sep. 13, 2018

(65) Prior Publication Data
US 2021/0139575 A1 May 13, 2021

(30) Foreign Application Priority Data

Mar. 7, 2017 (CN) .......................... 201710130518.0

(51) Int. Cl.
| | | |
|---|---|---|
| C07K 16/22 | (2006.01) | |
| A61K 39/00 | (2006.01) | |
| A61K 47/68 | (2017.01) | |

(52) U.S. Cl.
CPC .......... *C07K 16/22* (2013.01); *A61K 47/6803* (2017.08); *A61K 2039/505* (2013.01); *C07K 2317/31* (2013.01)

(58) Field of Classification Search
None
See application file for complete search history.

(56) References Cited

FOREIGN PATENT DOCUMENTS

| CN | 103012589 A | 4/2013 |
|---|---|---|
| CN | 103333247 A | 10/2013 |
| CN | 103965355 A | 8/2014 |
| CN | 103965356 A | 8/2014 |
| CN | 105646710 A | 6/2016 |
| CN | 106674349 A | 5/2017 |
| WO | 03075840 A2 | 9/2003 |

OTHER PUBLICATIONS

James D. Marks et. al. "By-passing immunization: Building high affinity human antibodies by chain shuffling" Biotechnology. The International Monthly for Industrial Biology>, Nature Publishing Group, US, vol. 10, No. 7, Jul. 1, 1992 (Jul. 1, 1992), pp. 779-783.
Dan Lu et. al. "Tailoring in vitro selection for a picomolar affinity humanantibody directed against vascular endothelial growth factor receptor 2 for enhanced neutralizing activity" <Journal of Biological Chemistry>, American Society for Biochemistry and Molecular Biology, US, vol. 278, No. 44,Oct. 31, 2003 (Oct. 31, 2003), pp. 43496-43507.
Dan Lu et. al. "Selection of high affinity human neutralizing antibodies to VEGFR2 from a large antibody phage display library for antiangiogenesis therapy" <International Journal of Cancer>, John Wiley & Sons, Inc, US, vol. 97, Jan. 1, 2002 (Jan. 1, 2002), pp. 393-399.
Hennie R, Hoogenboom et. al. "Natural and designer binding sites made by phage display technology" <Immunology TGDAY, Elsevier Publications>,Cambridge, GB,vol. 21, No. 8, Aug. 1, 2000 (Aug. 1, 2000), pp. 371-378.
Ruei-Min Lu et. al. "Novel human Ab against vascular endothelial growth factor receptor 2 shows therapeutic potential for leukemia and prostate cancer" <Cancer Science>,vol. 110, No. 12, Dec. 17, 2019 (Dec. 17, 2019), pp. 3773-3787.

*Primary Examiner* — Marianne P Allen
(74) *Attorney, Agent, or Firm* — Gang Yu (57) ABSTRACT

The application belongs to the technical field of biomedicines and provides an improved anti-Vascular Endothelial Growth Factor Receptor-2 (VEGFR-2) monoclonal antibody and an application thereof. By a computer-aided simulation design, a novel phage antibody library is designed, and an improved anti-VEGFR-2 monoclonal antibody is obtained after multiple rounds of screening. Both affinity and biological activity of the antibody are higher than those of an original antibody. The antibody is capable of effectively inhibiting combination of VEGFR-2 and a ligand Vascular Endothelial Growth Factor (VEGF) thereof in vitro, and may be used in treating a tumor and a disease caused by angiogenesis such as macular degeneration.

3 Claims, 3 Drawing Sheets
Specification includes a Sequence Listing.

ANTI-VEGFR-2 MONOCLONAL ANTIBODY

CROSS-REFERENCE TO RELATED PATENT APPLICATIONS

The present application is a National Stage of International Patent Application No: PCT/CN2018/076847, filed on Feb. 14, 2018, which claims the benefit of priority to Chinese Patent Application No. 201710130518.0, filed Mar. 7, 2017, which are incorporated by reference in their entirety herein.

SEQUENCE LISTING

The instant application contains a Sequence Listing which has been submitted electronically in ASCII format and is hereby incorporated by reference in its entirety. Said ASCII copy is named PN113091_Sequence_listing.txt and is 8151.04 bytes in size.

TECHNICAL FIELD

The disclosure relates to the technical field of bio-pharmaceuticals, and in particular to an improved anti-Vascular Endothelial Growth Factor Receptor-2 (VEGFR-2) monoclonal antibody.

BACKGROUND

The situation that tumor growth depends on formation of new vessels is already incisively studied in tumor biologics. Oxygen, nutrient substances, growth factors, hormone and proteolytic enzymes may be provided from angiogenesis, then tumor cells may be promoted to diffuse and transfer far away, and tumor growth and progression may be accelerated. Angiogenesis is a highly complex dynamic process and is regulated by multiple promote/anti-angiogenesis molecules. On/off of angiogenesis is regarded as a malignant marker that promote-angiogenesis surpasses anti-angiogenesis. A Vascular Endothelial Growth Factor/Vascular Endothelial Growth Factor Receptor (VEGF/VEGFR) axle triggers multiple signal networks, and thus epithelial cell survival, mitosis, transferring and differentiation, vascular permeability, VEGF and receptors thereof play a center role in normal and pathological angiogenesis. In multiple tumors of human beings, it verifies that additional tumor angiogenesis and the expression of tumor promote angiogenesis factor are related to tumor classification and malignancy.

Vascular endothelial cell growth factor (VEGF) is also called as a vascular permeability factor, is a specific mitosis source of endothelial cells and is also an effective angiogenesis and permeability induction factor, identified corresponding receptors are VEGFR-1 (Flt-1, FMS-like tyrosine 1), VEGFR-2 (which is also called as KDR/Flk-1, kinase insert domain-containing receptor, fetal liver kinase-1), VEGFR-3(Flt4), neurofilament protein-1 (neuropilin-1), neurofilament protein-2. VEGFR-2 is a main VEGF receptor on vascular endothelial cells and is a glycoprotein, an extracellular region of the receptor has seven immunoglobulin-like regions (including ligand binding domains and receptor dimerization structure domains), a tyrosine kinase catalysis structure domain is intracellular inserted, and the receptor is mainly expressed on endothelial cells and other cells such as megakaryocyte, retina ancestor cells, mesenchymal stem cells, and tumor cells such as melanoma cells, brain tumors and leukemia cells. As key molecules in vascular endothelial cell specific factor signaling transduction pathway, VEGF and VEGFR-2 receptors participate in generation of novel vessels of tumors, main biological functions of VEGF are achieved through VEGFR-2, VEGFR-2 and VEGF are transformed into dimers after binding, and intracellular tyrosine residues in VEGFR-2 are subjected to self-phosphorylation, so that cytomembrane/cytoplasm kinase cascade reaction signals are activated and transmitted into cell nucleus, a series of changes of the endothelial cells may be resulted, including vascular endothelial cell proliferation, survival, cytoskeleton rearrangement, cell migration, gene expression and the like, and blood vessel hyperplasia is caused ultimately.

Because of the key function of VEGF/VEGFR2 signaling pathway in occurrence and development of tumors, a great number of medicines for VEGF/VEGFR2 signaling pathway are available, such as an anti-VEGF antibody bevacizumab and an anti-VEGFR-2 antibody ramucirumab.

Antibodies are medicines with the highest technology contents and largest difficulties in biomedicines, and from the year of 2012, six of top ten single medicines in global sales are antibody medicines, so that the antibody medicines have great development potential in the market. A phage antibody library technology is the most common technology in antibody medicine screening, the phage antibody library technology is a new technology developed from phage display technology in gene antibody engineering, a gene pool with all antibody variable region genes of different species may be converted into a protein library displayed on the surface of phage, not only a monoclonal antibody is conveniently, rapidly and efficiently produced in vitro, but also a novel way is developed for monoclonal antibody humanization, and development of human monoclonal antibody production is promoted. In the patent CN103333247 B of our company, a series of VEGFR-2 antibodies were screened and obtained by using computer aided design and phage antibody technology, a basis is made to acquire anti-VEGFR-2 antibody medicines, and further study of our company shows that affinity, biological activity and the like of the antibodies provided in the patent may be further improved, so that on the basis, the antibodies are improved and optimized on original base.

SUMMARY

The disclosure provides an improved anti-Vascular Endothelial Growth Factor Receptor-2 (VEGFR-2) monoclonal antibody; according to the disclosure, two antibodies with the highest affinity in the patent CN103333247B are adopted as templates for computer aided simulation design, a new phage antibody library is designed, and a novel anti-VEGFR-2 monoclonal antibody of which both the affinity and the bioactivity are better than those of original patent antibodies are obtained through multiple rounds of screening.

To achieve the above purpose, the disclosure provides an improved anti-VEGFR-2 monoclonal antibody, including:

a light chain variable region and a heavy chain variable region, wherein an amino acid sequence of the light chain variable region includes any one of SEQ ID NO:1, SEQ ID NO:2 or SEQ ID NO:3; an amino acid sequence of the heavy chain variable region includes SEQ ID NO:4.

The disclosure further provides an antibody, a polypeptide or a protein comprising the light chain variable region or the heavy chain variable region.

The disclosure further provides a polynucleotide sequence or a combination encoding the amino acid sequences of the light chain variable region or the heavy chain variable region.

The disclosure further provides a recombinant Deoxyribonucleic Acid (DNA) expression vector comprising the polynucleotide sequence or the combination; the recombinant DNA expression vector includes DNA sequences for encoding amino acid sequences of a heavy chain variable region, a heavy chain constant region, a light chain variable region and a light chain constant region of anti-VEGFR-2 monoclonal antibody.

The disclosure further provides a host cell for transfecting the recombinant DNA expression vector, and the host cell includes a mammalian cell, an insect cell, *Escherichia coli* or yeast, preferably the mammalian cell, and further preferably an HEK293E cell, a Chinese Hamster Ovary (CHO) cell or an NSO cell.

The heavy chain constant region of the disclosure is selected from the group consisting of human IgG1, IgG2, IgG3 and IgG4 or the group consisting of mouse IgG1, IgG2a and IgG2b.

The disclosure further provides a complete antibody or a fragment comprising the light chain variable region and the heavy chain variable region, the fragment is an anti-VEGFR-2 monoclonal antibody, and the fragment includes, but not limited, Fab, Fab', F(ab')$_2$, Fv or ScFv.

The disclosure further provides a single-chain antibody, a single domain antibody, a bispecific antibody, an antibody medicine conjugate and chimeric antigen receptor T cell immunotherapy comprising the amino acid sequence of the light chain variable region or the heavy chain variable region.

The disclosure further provides a monoclonal antibody, an artificial vector, a medicine or a medicine composition comprising the light chain variable region or the heavy chain variable region.

The disclosure further provides a detection reagent or a detection kit comprising the light chain variable region or the heavy chain variable region.

The antibody may be used for treating diseases caused by angiogenesis, and the diseases include, but not limited, tumors and macular degeneration.

Wherein ScFv is a single-chain fragment variable; the HEK293E cell is a human embryonic kidney 293E cell; the CHO cell is a Chinese hamster ovary cell; the NSO cell is a mouse NSO thymoma cell.

Compared with the prior art, the disclosure has the following advantages.

The anti-VEGFR-2 monoclonal antibody which has higher affinity, is capable of well inhibiting binding of VEGFR-2 and a ligand Vascular Endothelial Growth Factor (VEGF) thereof in vitro, has good bioactivity in vitro and has wide development prospect.

The anti-VEGFR-2 monoclonal antibody provided by the disclosure is used for treating diseases caused by tumor angiogenesis, including, but not limited, cancers such as non-small cell lung cancer, metastatic non-small cell lung cancer, gliomas, colorectal cancer, hepatocellular carcinoma, metastatic hepatocellular carcinoma, metastatic breast cancer with negative Human Epidermal Growth Factor Receptor (HER2), metastatic gastric adenocarcinoma, metastatic colorectal cancer, metastatic melanoma and metastatic renal cell carcinoma, and diseases such as macular degeneration.

DETAILED DESCRIPTION OF THE EMBODIMENTS

Detailed implementation methods of the disclosure are shown in embodiments, and methods and reagents in the embodiments are all common testing methods and reagents unless otherwise specified. The embodiments are only used for describing and interpreting the disclosure, but do not constitute improper limitations to the disclosure.

The disclosure provides an improved anti-Vascular Endothelial Growth Factor

```
(VEGFR-2 light chain variable region
sequence 1):
                                   SEQ ID NO: 1
DIQMTQSPSSVSASIGDRVTITCRASQAIDNVVLGVVYQQKPGKAPKLLI

YEGSNLNTGVPSRFSGSGSGTDFTLTISSLQAEDFAVYFCQQAKSFPPTF

GGGTKVDIK;

(VEGFR-2 light chain variable region
sequence 2):
                                   SEQ ID NO: 2
DIQMTQSPSSVSASIGDRVTITCRASDAIDQVVLGVVYQQKPGKAPKLLI

YEASNLDTGVPSRFSGSGSGTDFTLTISSLQANQFAVYFCQQAKSFPPTF

GGGTKVDIK;

(VEGFR-2 light chain variable region
sequence 3):
                                   SEQ ID NO: 3
DIQMTQSPSSVSASIGDRVTITCRASQGIDQVVLGVVYQQKPGKAPKLLI

YEGSNLNTGVPSRFSGSGSGTDFTLTISSLQANQFAVYFCQQAKSFPPTF

GGGTKVDIK;

(VEGFR-2 heavy chain variable region
sequence 1):
                                   SEQ ID NO: 4
QVQLVESGGGLVKPGGSLRLSCAASAFTFSSYSMNVVVRQAPGKGLEVVV

SSISSSSSYIYYADSVKGRFTISRDNAKNSLYLQMNSLRAEDTAVYYCAR

VTDAFDLVVGQGTMVTVSS.
```

Preferably, the disclosure further provides an antibody, a polypeptide or a protein comprising the light chain variable region or the heavy chain variable region.

More preferably, the disclosure further provides a polynucleotide sequence or a combination encoding the amino acid sequences of the light chain variable region or the heavy chain variable region.

More preferably, the disclosure further provides a recombinant Deoxyribonucleic Acid (DNA) expression vector comprising the polynucleotide sequence or the combination; the recombinant DNA expression vector includes DNA sequences for encoding a heavy chain variable region, a heavy chain constant region, a light chain variable region and a light chain constant region of the anti-VEGFR-2 monoclonal antibody.

More preferably, the disclosure further provides a host cell for transfecting the recombinant DNA expression vector, and the host cell includes a mammalian cell, an insect cell, *Escherichia coli* or yeast, preferably the mammalian cell, and further preferably an HEK293E cell, a Chinese Hamster Ovary (CHO) cell or an NS0 cell.

More preferably, the heavy chain constant region of the disclosure is selected from the group consisting of human IgG1, IgG2, IgG3 and IgG4 or the group consisting of mouse IgG1, IgG2a and IgG2b.

More preferably, the disclosure further provides a complete antibody or a fragment comprising the light chain variable region and the heavy chain variable region, the fragment of an anti-VEGFR-2 monoclonal antibody, and the fragment includes, but not limited, Fab, Fab', F(ab')$_2$, Fv or ScFv.

More preferably, the disclosure further provides a single-chain antibody, a single domain antibody, a bispecific antibody, an antibody medicine conjugate and chimeric antigen receptor T cell immunotherapy comprising the amino acid sequence of the light chain variable region or the heavy chain variable region.

More preferably, the disclosure further provides a monoclonal antibody, an artificial vector, a medicine or a medicine composition comprising the light chain variable region or the heavy chain variable region.

More preferably, the monoclonal antibody is a full-human antibody.

More preferably, the disclosure further provides a detection reagent or a detection kit comprising the light chain variable region or the heavy chain variable region.

More preferably, the antibody may be used for treating diseases caused by angiogenesis, including, but not limited, cancers such as non-small cell lung cancer, metastatic non-small cell lung cancer, gliomas, colorectal cancer, hepatocellular carcinoma, metastatic hepatocellular carcinoma, metastatic breast cancer with negative Human Epidermal Growth Factor Receptor (HER2), metastatic gastric adenocarcinoma, metastatic colorectal cancer, metastatic melanoma and metastatic renal cell carcinoma, and diseases such as macular degeneration.

Detailed Embodiments

The disclosure is specifically described with drawings and embodiments.

Embodiment 1 Biopanning of Anti-VEGFR-2 Single-Chain Antibodies

Figure 1:
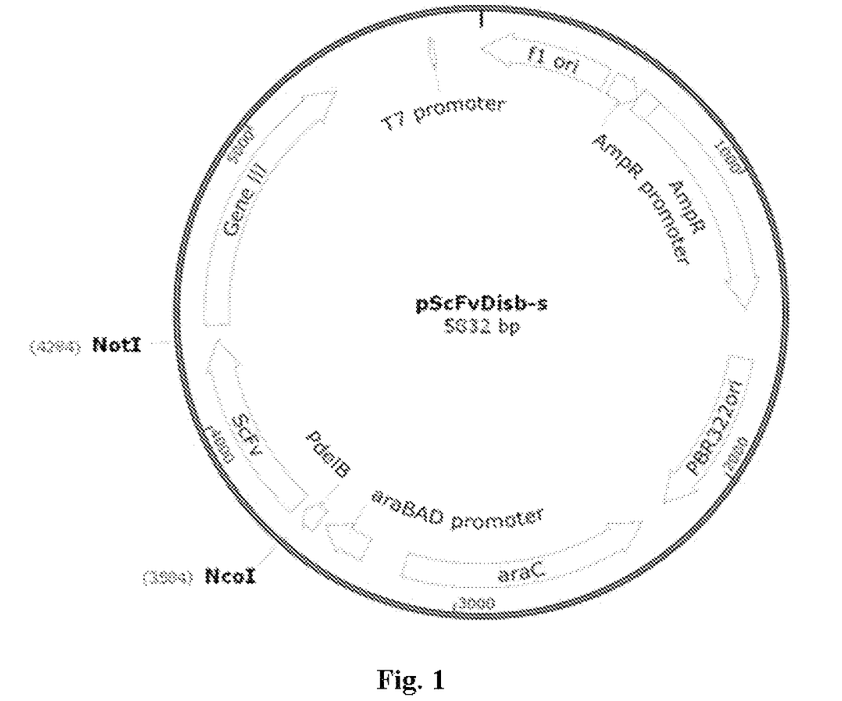
FIG. 1 shows a pScFvDisb-S plasmid profile.

A pCom3 vector (purchased from the Biovector Science Lab, Inc.) is modified with a series of gene cloning methods, and thus the vector may be applied to construction and expression of a phage single-chain antibody library. The modified vector is named as pScFvDisb-S, a plasmid profile of the vector is as shown in FIG. 1, and based on the vector, a novel total synthetic phage antibody library based on antibody sequences in patent CN10333247B is constructed.

Coat an immune tube by VEGFR-2 extracellular region as an antigen, the antigen coating amount is 2 ug/500 ul/tube, and coat over night at 4 DEG C. Respectively seal the immune tube and the total synthetic phage antibody library with 4% degreased milk powder/Phosphate Buffered Tween Solution (PBST), and seal for one hour at the room temperature. Put the sealed phage antibody library into the immune tube for antigen-antibody binding, the amount of the phage is about $10^9$-$10^{12}$, and react for 1 hour at the room temperature. Wash a few times with PBST-Phosphate Buffered Solution (PBST-PBS) to remove phages which are not binding, elute with 0.1 M PH2.2 glycine, and neutralize eluted phage antibody solution with 1.5M PH8.8 Tris-HCl till a pH value is about 7.0.

Infect the neutralized phage with 10 ml of TG1 bacterium solution growing to a logarithmic phase, leave to stand for 30 minutes in an incubator at 37 DEG C., take out a part of the bacterium solution for gradient dilution and coat a 2YTAG plate, for calculating a phage yield. Centrifuge the residual bacterium solution to remove supernate, resuspend bacterium in a small amount of medium, suck out, and coat a large 2YTAG plate fora next round of screening.

Scrape off the bacterium which is infected and applied to the plate from the large plate, inoculate with 2YTAG liquid medium, shake till the logarithmic phase, add M13 helper phage for super-infection, culture over night at 28 DEG C. to amplify the phage, precipitate and purify the phage with PEG6000-NaCl for a next round of screening, and enrich and screen the phage library for three times in total.

Embodiment 2 Identification of Positive Cloning of Anti-VEGFR-2 Phage Single-Chain Antibody After three rounds of screening, select monocolonies with good partitioning, inoculate with a deep 96-pore plate with the 2YTAG liquid medium, culture at 37 DEG C. at 220 rpm till the logarithmic phase, add about $10^{10}$ of the helper phage M13K07 into each pore, and leave to stand and infect for 30 minutes at 37 DEG C. Centrifuge at 4000 rpm for 15 minutes at 4 DEG C., abandon supernate, resuspend and precipitate the bacterium with 2YTAK, and culture over night at 28 DEG C. at 220 rpm. Suck supernate with the phage to carry out Enzyme Linked Immunosorbent Assay (ELISA) identification, the phage comprising a biological antibody sequence (an amino acid sequence of heavy chain is the sequence No. 3 in CN10333247B, and an amino acid sequence of light chain is the sequence No. 9 in CN10333247B) with a same vector and a same construction method of CN10333247B is used as positive control (named as 0-1), screen to obtain monoclonal antibodies N–1, N–2 and N–3 with high affinity, and carry out gene sequencing to confirm the antibodies are different from sequences in the original patent CN10333247B.

Embodiment 3 Gradient Dilution Phage ELISA to Compare Affinity of Anti-VEGFR-2 Single-Chain Antibodies Display and purify the monocolonies obtained in the embodiment 2, and carry out phage gradient dilution ELISA to test and identify affinity.

Figure 2:
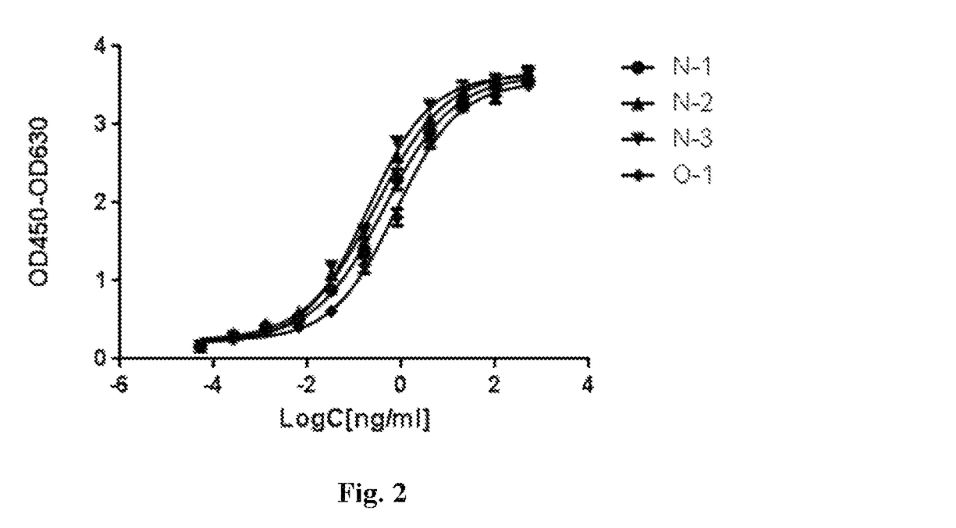
FIG. 2 shows relative affinity of anti-VEGFR-2 single-chain antibody in gradient ELISA comparison.

Coat VEGFR-2 extracellular region with a pH 9.6 carbonate buffer solution, and coat over night with 20 ng/pore/100 ul at 4 DEG C. Wash three times with PBST, and seal for 1 hour with 4% milk-PBST at 37 DEG C. Dilute the purified phage with 4% milk-PBST Five-fold-gradient, put 100 ul of diluted sample into each pore, and leave to stand for 1 hour at the room temperature. Wash ELISA plate with PBST, put an HRP-anti-M13 monoclonal antibody which is diluted with 4% milk-PBST into the ELISA plate, and leave to stand for 1 hour at the room temperature. Develop with a Tetramethylbenzidine (TMB) developing kit for 10 minutes at the room temperature. Terminate with 2M $H_2SO_4$, and read numbers at 450 nm/630 nm. Results are shown in FIG.

2, and three screened different single-chain antibodies all can specifically bind with VEGFR-2, and the binding capabilities are all higher than that of conventional 0-1.

Embodiment 4 Preparation of Complete Anti-KDR Antibodies

Figure 3:
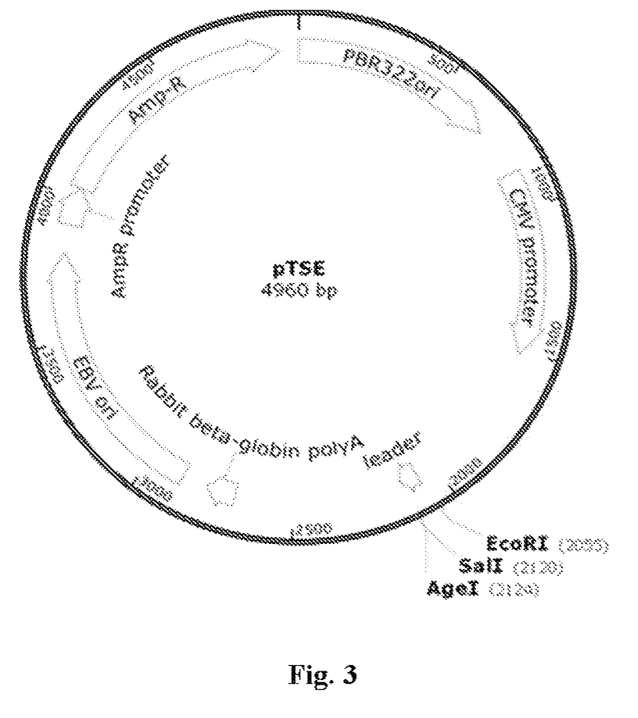
FIG. 3 shows a protein expressed pTSE plasmid profile.

Respectively clone genes of a heavy chain VH and a light chain κ of the three antibodies N−1, N−2 and N−3 into a vector pTSE (as shown in FIG. 3) comprising constant region genes of heavy chain and light chain, and a vector pTSE for encoding a human IgG1 constant region (see SEQ ID NO: 5) and a constant region of the chain κ (see SEQ ID NO: 6) (the vector pTSE is as shown in FIG. 3, and see preparation processes in paragraph [0019] on page 3 of the specification of CN103525868A).

```
(constant region sequence of human IgG1):
                                         SEQ ID NO: 5
ASTKGPSVFPLAPSSKSTSGGTAALGCLVKDYFPEPVTVSVVNSGALTSG

VHTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVDV

SHEDPEVKFNVVYVDGVEVHNAKTKPREEQYNSTYRVVSVLTVLHQDVVL

NGKEYKCKVSNKALPAPIEKTISKAKGQPREPQVYTLPPSRDELTKNQVS

LTCLVKGFYPSDIAVEVVESNGQPENNYKTTPPVLDSDGSFFLYSKLTVD

KSRVVQQGNVFSCSVMHEALHNHYTQKSLSLSPG.

(constant region sequence of chain κ):
                                         SEQ ID NO: 6
RTVAAPSVFIFPPSDEQLKSGTASVVCLLNNFYPREAKVQVVKVDNALQS

GNSQESVTEQDSKDSTYSLSSTLTLSKADYEKHKVYACEVTHQGLSSPVT

KSFNRGEC.
```

Carry out a transient transfection on an HEK293E cell to express the complete antibody, purify with an AKTA instrument protein A affinity column to obtain a complete antibody protein, and test a protein concentration with a Bicinchoninic Acid Disodium (BCA) kit.

Figure 4:
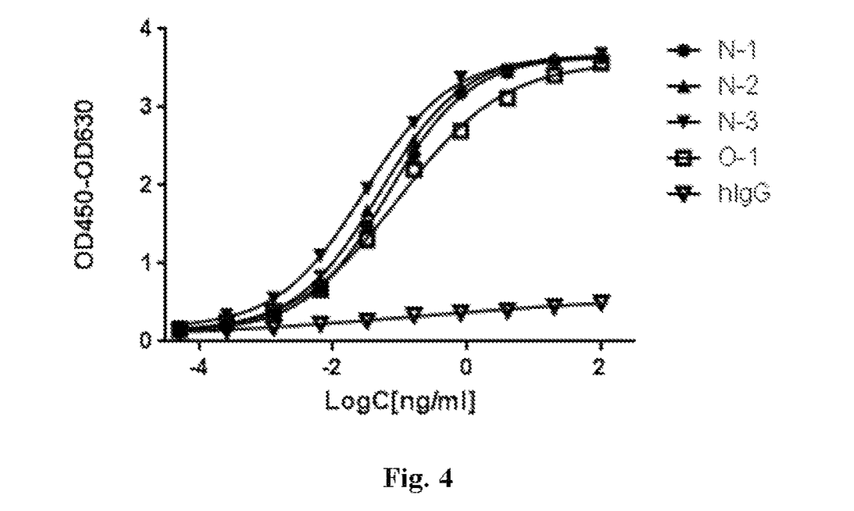
FIG. 4 shows comparison of binding capabilities of anti-VEGFR-2 monoclonal antibodies with KDR.

Embodiment 5 Binding Experiment of Complete Antibody and VEGFR2 Extracellular Region Coat VEGFR extracellular region with a pH9.6 carbonate buffer solution, and coat over night with 20 ng/pore/100 ul at 4 DEG C. Wash three times with 300 ul/pore/PBST, and further seal for 1 hour with 4% milk-PBST at 37 DEG C., and add complete antibodies labeled with biotin of different dilution degrees. Use human IgG(hIgG) as a homotype control, the highest concentration of various complete antibodies is 100 ng/ml, make 8 gradients with 5 times of dilution, and incubate for 2-3 hours at 37 DEG C. Wash five times with 300 ul/pore PBST, and further incubate for 1 hour with streptavidin of 4% milk-PBST diluted in a ratio of 1:10000 at 37 DEG C. Wash eight times with 300 ul/pore PBST, develop with the TMB developing kit with 100 ul/pore for 10 minutes at the room temperature, and terminate with 2M $H_2SO_4$. Read numbers at 450 nm/630 nm. Results are shown in FIG. 4, all antibodies may well bind with KDR molecules on cell surface, N3 has the highest affinity, and the affinity of N−1, N−2 and N−3 is higher than that of conventional 0-1.

Figure 5:
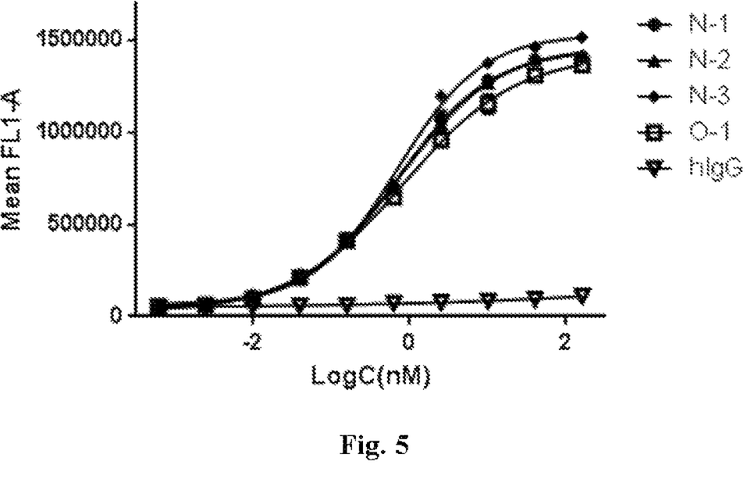
FIG. 5 shows binding of antibodies of the disclosure with VEGFR-2 on cell surface.

Embodiment 6 Analysis on Binding Specificity of Complete Antibodies and VEGFR-2 on Cell Surface According to the disclosure, binding of different bispecific antibodies with VEGFR-2 on cell surface is detected using CHO cells with over-expression of VEGFR-2, and human IgG (hIgG) is used as a homotype control. Digest with 0.25% pancreatin, and centrifuge to collect cells. At the same time dilute various antibodies, and dilute with a highest concentration of 100 nM with a 4-fold gradient. Wash collected cells with PBS+1% BSA for three times, further add PBS+1% BSA to resuspend the cells, lay the cells into a 96-pore plate, put $1 \times 10^5$ cells into each pore, add 100 ul of the diluted bispecific antibodies, and incubate for 1 hour at the room temperature; centrifuge to remove supernate, wash for three times with PBS, further resuspend the cells with diluted anti-human IgG FC antibody marked by Alexa488, then incubate for 1 hour without light at the room temperature, wash for three times with PBS, resuspend with 100 ul of PBS, and detect a fluorescence intensity with a flow cytometry. Analyze results with Graphpad Prism. Results show that N3 is capable of better binding with VEGFR-2 expressed by the cells, and the binding capabilities of N1, N2 and N3 are all better than 0-1 (see FIG. 5).

Figure 6:
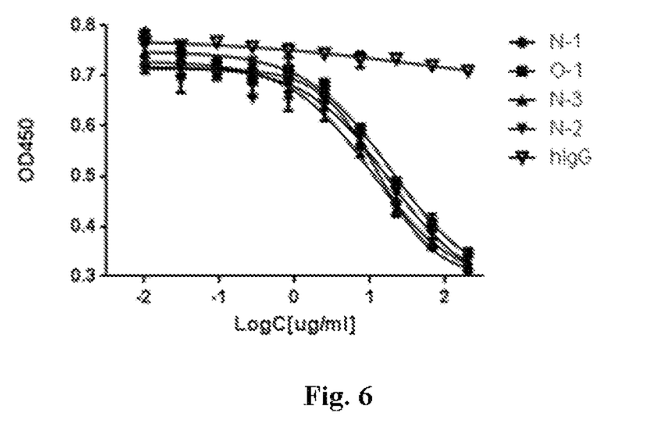
FIG. 6 shows a proliferation inhibition effect of the antibodies in the disclosure on human umbilical vein endothelial cell (HUVEC).

Embodiment 7 Experiment of Human Umbilical Vein Endothelial Cell (HUVEC) Proliferation Inhibition of Complete Antibodies Human umbilical vein endothelial cell (HUVEC) is already widely applied to study on vascular endothelial cell proliferation, cell signalling pathways and multiple tumorigenesis mechanisms, and the disclosure studies HUVEC proliferation inhibitions with different anti-VEGFR-2 antibodies. When HUVECs grow to an abundance of 80%, replace a medium by a fresh EGM medium with 5% of FBS, digest with pancreatin 6 hours later, further wash digested cells for 4-5 times with a serum-free medium, completely pour off the medium as much as possible after each time of centrifugation, count resuspension cells, inoculate 5000 cells/pore into a 96-pore plate, avoid edge pores of the 96-pore plate, pour 100 ul of the serum-free medium into each pore, and carry out hunger over-night treatment. Suck off supernate 14-16 hours later, add 50 ul of VEGF/ECM (200 ng/ml) till a concentration is 100 ng/ml, uniformly mix with different antibodies of different concentrations, and culture for 24 hours. Further add CCK-8, and detect cell proliferation. Results show that $IC_{50}$ (ng/L) of N1, N2 and N3 is 12.76, 17.32 and 10.53 respectively, and $IC_{50}$ (ng/L) of 0-1 is 18.59; human umbilical vein endothelial cell proliferation inhibition capabilities of N1, N2 and N3 are all higher than 0-1, and N3 has the best proliferation inhibition capability (see FIG. 6). Embodiments 5-7 show that results of both molecular and cytology levels of N1, N2 and N3 are better than 0-1 of an optimal antibody of the original patent CN103525868A, and it means that candidate molecules of the patent have good development and application prospects.

The antibody may be used for treating diseases caused by tumor angiogenesis, including, but not limited, cancers such as non-small cell lung cancer, metastatic non-small cell lung cancer, gliomas, colorectal cancer, hepatocellular carcinoma, metastatic hepatocellular carcinoma, metastatic breast cancer with negative HER2, metastatic gastric adenocarcinoma, metastatic colorectal cancer, metastatic melanoma and metastatic renal cell carcinoma, and diseases such as macular degeneration.

For those of ordinary skill in the art, the embodiments only exemplarily describe the disclosure, and obviously specific realizations of the disclosure are not limited to the modes above mentioned. Any non-substantive improvement on the basis of the ideas and technical schemes of the disclosure, or applications of the ideas and the technical schemes of the disclosure without improvement to other situations shall fall within the scope of protection of the disclosure.

What is claimed is:

1. An anti-VEGFR-2 monoclonal antibody, comprising a light chain variable region and a heavy chain variable region, wherein an amino acid sequence of the light chain variable region comprises any one of SEQ ID NO:1, SEQ ID NO:2 or SEQ ID NO:3; and an amino acid sequence of the heavy chain variable region comprises SEQ ID NO:4.

2. The monoclonal antibody as claimed in claim 1, wherein the anti-VEGFR-2 monoclonal antibody further comprises a heavy chain constant region, and the heavy chain constant region is selected from the group consisting of human IgG1, IgG2, IgG3 and IgG4 or the group consisting of mouse IgG1, IgG2a and IgG2b.

3. A detection kit comprising the anti-VEGFR-2 monoclonal antibody as claimed in claim 1 and a detection reagent.

* * * * *

```
                            SEQUENCE LISTING

<160> NUMBER OF SEQ ID NOS: 6

<210> SEQ ID NO 1
   <211> LENGTH: 107
   <212> TYPE: PRT
   <213> ORGANISM: Homo sapiens

<400> SEQUENCE: 1

Asp Ile Gln Met Thr Gln Ser Pro Ser Ser Val Ser Ala Ser Ile Gly
   1               5                   10                  15

Asp Arg Val Thr Ile Thr Cys Arg Ala Ser Gln Ala Ile Asp Asn Trp
                   20                  25                  30

Leu Gly Trp Tyr Gln Gln Lys Pro Gly Lys Ala Pro Lys Leu Leu Ile
               35                  40                  45

Tyr Glu Gly Ser Asn Leu Asn Thr Gly Val Pro Ser Arg Phe Ser Gly
       50                  55                  60

Ser Gly Ser Gly Thr Asp Phe Thr Leu Thr Ile Ser Ser Leu Gln Ala
   65                  70                  75                  80

Glu Asp Phe Ala Val Tyr Phe Cys Gln Gln Ala Lys Ser Phe Pro Pro
                   85                  90                  95

Thr Phe Gly Gly Gly Thr Lys Val Asp Ile Lys
               100                 105

<210> SEQ ID NO 2
   <211> LENGTH: 107
   <212> TYPE: PRT
   <213> ORGANISM: Homo sapiens

<400> SEQUENCE: 2

Asp Ile Gln Met Thr Gln Ser Pro Ser Ser Val Ser Ala Ser Ile Gly
   1               5                   10                  15

Asp Arg Val Thr Ile Thr Cys Arg Ala Ser Asp Ala Ile Asp Gln Trp
                   20                  25                  30

Leu Gly Trp Tyr Gln Gln Lys Pro Gly Lys Ala Pro Lys Leu Leu Ile
               35                  40                  45

Tyr Glu Ala Ser Asn Leu Asp Thr Gly Val Pro Ser Arg Phe Ser Gly
       50                  55                  60

Ser Gly Ser Gly Thr Asp Phe Thr Leu Thr Ile Ser Ser Leu Gln Ala
   65                  70                  75                  80

Asn Gln Phe Ala Val Tyr Phe Cys Gln Gln Ala Lys Ser Phe Pro Pro
                   85                  90                  95

Thr Phe Gly Gly Gly Thr Lys Val Asp Ile Lys
               100                 105

<210> SEQ ID NO 3
   <211> LENGTH: 107
   <212> TYPE: PRT
   <213> ORGANISM: Homo sapiens

<400> SEQUENCE: 3

Asp Ile Gln Met Thr Gln Ser Pro Ser Ser Val Ser Ala Ser Ile Gly
   1               5                   10                  15
```

-continued

Asp Arg Val Thr Ile Thr Cys Arg Ala Ser Gln Gly Ile Asp Gln Trp
                20                  25                  30

Leu Gly Trp Tyr Gln Gln Lys Pro Gly Lys Ala Pro Lys Leu Leu Ile
            35                  40                  45

Tyr Glu Gly Ser Asn Leu Asn Thr Gly Val Pro Ser Arg Phe Ser Gly
 50                  55                  60

Ser Gly Ser Gly Thr Asp Phe Thr Leu Thr Ile Ser Ser Leu Gln Ala
 65                  70                  75                  80

Asn Gln Phe Ala Val Tyr Phe Cys Gln Gln Ala Lys Ser Phe Pro Pro
                85                  90                  95

Thr Phe Gly Gly Gly Thr Lys Val Asp Ile Lys
            100                 105

<210> SEQ ID NO 4
<211> LENGTH: 116
<212> TYPE: PRT
<213> ORGANISM: Homo sapiens

<400> SEQUENCE: 4

Gln Val Gln Leu Val Glu Ser Gly Gly Gly Leu Val Lys Pro Gly Gly
 1               5                  10                  15

Ser Leu Arg Leu Ser Cys Ala Ala Ser Ala Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Val Thr Asp Ala Phe Asp Leu Trp Gly Gln Gly Thr Met Val
                100                 105                 110

Thr Val Ser Ser
        115

<210> SEQ ID NO 5
<211> LENGTH: 329
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 6
<211> LENGTH: 107
<212> TYPE: PRT
<213> ORGANISM: Homo sapiens

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105